(12) United States Patent
Del Rio et al.

(10) Patent No.: US 7,614,793 B2
(45) Date of Patent: Nov. 10, 2009

(54) NEEDLE/ROLLER BEARING

(75) Inventors: Eddy H. Del Rio, Royal Palm Beach, FL (US); Thomas E. Anspach, Jupiter, FL (US)

(73) Assignee: The Anspach Effort, Inc, Palm Beach Gardens, FL (US)

( * ) Notice: Subject to any disclaimer, the term of this patent is extended or adjusted under 35 U.S.C. 154(b) by 0 days.

(21) Appl. No.: 10/306,256

(22) Filed: Nov. 27, 2002

(65) Prior Publication Data

US 2004/0101225 A1    May 27, 2004

(51) Int. Cl.
  *F16C 19/49*    (2006.01)
(52) U.S. Cl. .................. 384/454; 384/553; 384/610
(58) Field of Classification Search ................. 384/548, 384/551, 553, 565, 610, 454, 463, 492
  See application file for complete search history.

(56) References Cited

U.S. PATENT DOCUMENTS

| 3,425,759 | A | * | 2/1969 | Schwarzschild | ............ 384/491 |
| 3,764,188 | A | * | 10/1973 | Suska | ............ 384/463 |
| 5,823,686 | A | * | 10/1998 | Murano et al. | ............ 384/492 |
| 6,367,982 | B1 | * | 4/2002 | Doi et al. | ............ 384/565 |

\* cited by examiner

*Primary Examiner*—Thomas R. Hannon
(74) *Attorney, Agent, or Firm*—Norman Friedland

(57) ABSTRACT

A needle bearing is designed for a high speed drill or MDA surgical instruments that include alternate rollers made from metallic and plastic or synthetic material mounted in the bore of the housing of the drill or MDA and the shaft being supported by the needle bearing. The inner race, outer race and/or cage may be eliminated from the assembly.

15 Claims, 3 Drawing Sheets

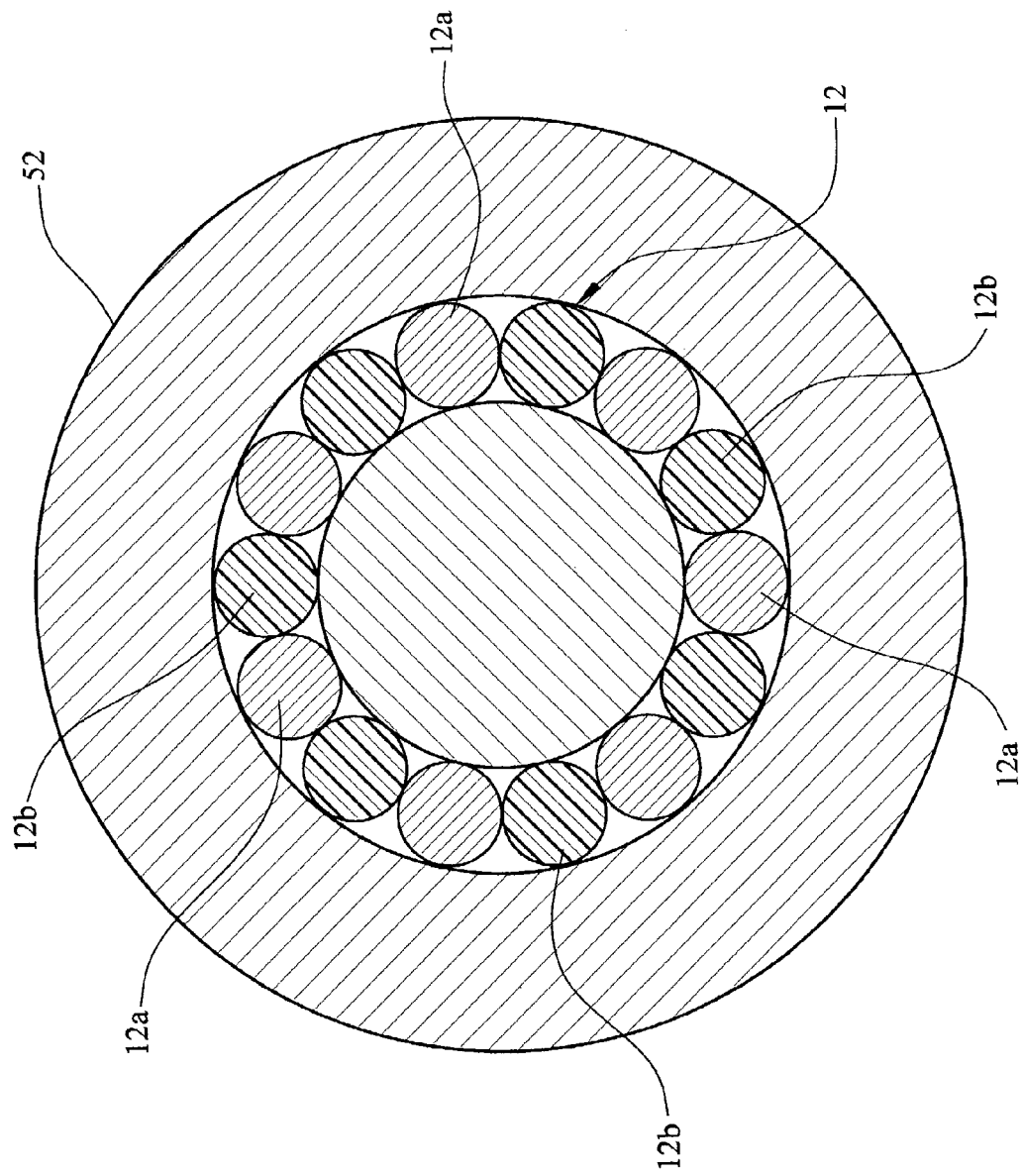

NEEDLE/ROLLER BEARING

TECHNICAL FIELD

This invention relates to bearings for high speed rotational machinery and particularly to needle/roller bearings.

BACKGROUND OF THE INVENTION

As is well known in medical instrumentation technology, the radial loads generated in high speed drills are typically taken up by ball bearings. Preferably roller or needle bearings serve to take up these radial loads, but at high speed operations these bearings tend to deteriorate or burn out quickly and hence, the life of the drills or drill attachments utilizing the roller or needle bearings are limited and cannot attain the high rotational speeds that are often desired.

Many of drills utilized for medical applications are typically supported by ball bearings and utilize pneumatic driven motors that operate at relative high speeds. These drills rotatably support cutters and the like that when used in a medical procedure, the surgeon has the propensity to move the cutter sideways, which, obviously, imposes heavy, and sometimes severe, radial loads. Examples of these drills are the Black Max® and eMax™ manufactured by The Anspach Effort, Inc. the assignee of this patent application, and for further details of these types of drills reference should be made thereto and these models are incorporated herein by reference Another example of bearings utilized for surgical instruments is disclosed and claimed in U.S. patent application Ser. No. 09/962,989 filed on Sep. 25, 2001 entitled "Bearings For Surgical Instruments" and assigned to the same assignee as this patent application, which is incorporated herein by reference. This patent application teaches the use of a journal bearing that replaces one of the bearings in the Micro Dissection Attachment (MDA) disclosed in this patent application. As taught in the aforementioned patent application, the journal bearing is made from a polymer of polyimide resin and graphite composition and is judiciously configured so that there are two points of contact of the mating surfaces. This bearing configuration allows for the miniaturizing of the MDA at the distal end so as to enhance the line of vision of the cutter for the surgeon to facilitate the procedure in surgery. The journal bearing of this teachings also enhances the wear characteristics of the MDA and has good characteristics for absorbing radial loads. Like the journal bearing as taught in the U.S. patent application Ser. No. 09/962,989, supra, the roller or needle bearing of this invention can be made sufficiently small so that it affords to the motor casing that is used as the handle the diameter of which is sufficiently small and affording to the surgeon a good feel for performing a surgical procedure, while enhancing the load characteristics of the instrument.

We have found that we can make diameter of the rollers of the needle/roller bearing of this invention substantially in the order of 0.0416 inch. Obviously, there are no limitation in the upper end of roller size of the bearing. Hence, for surgical instruments where the roller bearings only support radial loads, it is fundamentally important that the bearings sizes are small and factually, the smaller the bearing the better.

While ball bearings have been proven to be efficacious for many surgical instruments the needle or roller bearings are particularly efficacious for use in high speed drills and have advantages over the ball bearing when it is desirable to support the rotary shaft and take up the radial loads. This invention is intended to solve the problem noted in the above paragraphs by designing the needle/roller bearing so that alternate rollers of the bearing are made from metallic or ceramic material and the other alternate rollers are made from a non-metallic or ceramic material such as a plastic or a synthetic material. I have found that a stainless steel and a polyimide resin material or an alloy thereof combined with graphite material are particularly suited for these high speed rotary machines.

This invention contemplated utilizing the needle/roller bearing in these high speed surgical drills, as described above, and support the shaft in such a manner that the inner race, outer race and cage are eliminated. While the ball bearings described and claimed in U.S. patent application Ser. No. 10/153,368 filed on May 22, 2002, by Eddy Del Rio, entitled Ball Bearing are utilized for high speed drills and support the main drill shaft in the drill without the use of the inner race and outer race, it is believed that this arrangement of the needle/roller bearing with the absence of the inner race, outer race and cage of this invention has never been utilized heretofore.

As will be more evident in the description to follow, the needle/roller bearing of this invention is particularly efficacious when used in conjunction with a spherical thrust bearing. The invention lends itself to self-lubricate the rollers by mounting them in a sealed compartment containing a suitable grease or lubricant. This is true whether or not the thrust bearing is used in conjunction with the needle/roller bearing configuration.

We have found that bearings made in accordance with this invention affords the following characteristics although other characteristics may be realized:

1) The needle bearings are utilized without the races and hence, the overall envelope size is smaller in diameter than those utilizing races, enhancing the wear characteristics of the bearing;

2) the bearings are characterized as easy to manufacture, less expensive than heretofore known bearings, are maintenance free and are reliable and have a long operational life and particularly efficacious for high speed operation;

3) the material of the bearings can be any well known material, so long as alternate rollers are made from a metallic or ceramic material and the other alternate rollers are made from a non-metallic material or non-ceramic material;

4) pre-loading is not necessary;

5) the assembly and disassembly of the bearing are simplified in comparison to heretofore known needle bearings; and 6) misalignment of the rollers is obviated.

Moreover, tests have proven that drills manufactured utilizing bearings made in accordance with this invention have operated in high speeds that are typically utilized for these medical procedure without incurring any deficiencies.

The foregoing and other features of the present invention will become more apparent from the following description and accompanying drawings.

SUMMARY OF THE INVENTION

An object of this invention is to provide an improved radial bearing for a high speed surgical instrument.

A feature of this invention is to alternate the rollers of a needle bearing such that adjacent rollers are made from a metallic material and the other adjacent rollers are made from a plastic or synthetic material. A ceramic material can be substituted for the metallic material.

A feature of this invention is the fabricating of rollers for a needle bearing made from a metallic material taken from the group of ferrous material and stainless steel and made from a plastic material taken from the group of polymer of polyimide resin, polyimide resin and graphite composition.

Another feature of this invention is that the needle/roller bearing of this invention supports the shaft of a high speed rotary drill and absorbs the radial loads and is combined with a thrust ball bearing designed to absorb the thrust loads to attain an efficient high speed surgical drill. Any of the embodiments utilizing this invention may include a lubricant compartment housing the bearings that can be completely sealed to provide a self-lubricating system that will assure long life of the drill.

BRIEF DESCRIPTION OF THE DRAWINGS

FIG. 3 is a sectional view taken along lines 3-3 of FIG. 1.

These figures merely serve to further clarify and illustrate the present invention and are not intended to limit the scope thereof.

DETAILED DESCRIPTION OF THE INVENTION

This invention in its preferred embodiment is a surgical drill that utilizes an air driven motor for powering the cutter or other medical instrument utilized in surgical procedures and it should be obvious to anyone skilled in this technology that any surgical motor using various mediums can be utilized to power the cutter or other medical instruments. Moreover, the invention is being described utilizing Mini Max®, Black Max® and eMax™ motors which are products available from the assignee of this patent application, and it should be understood that other types of pneumatic motors could be substituted therefor.

Figure 1:
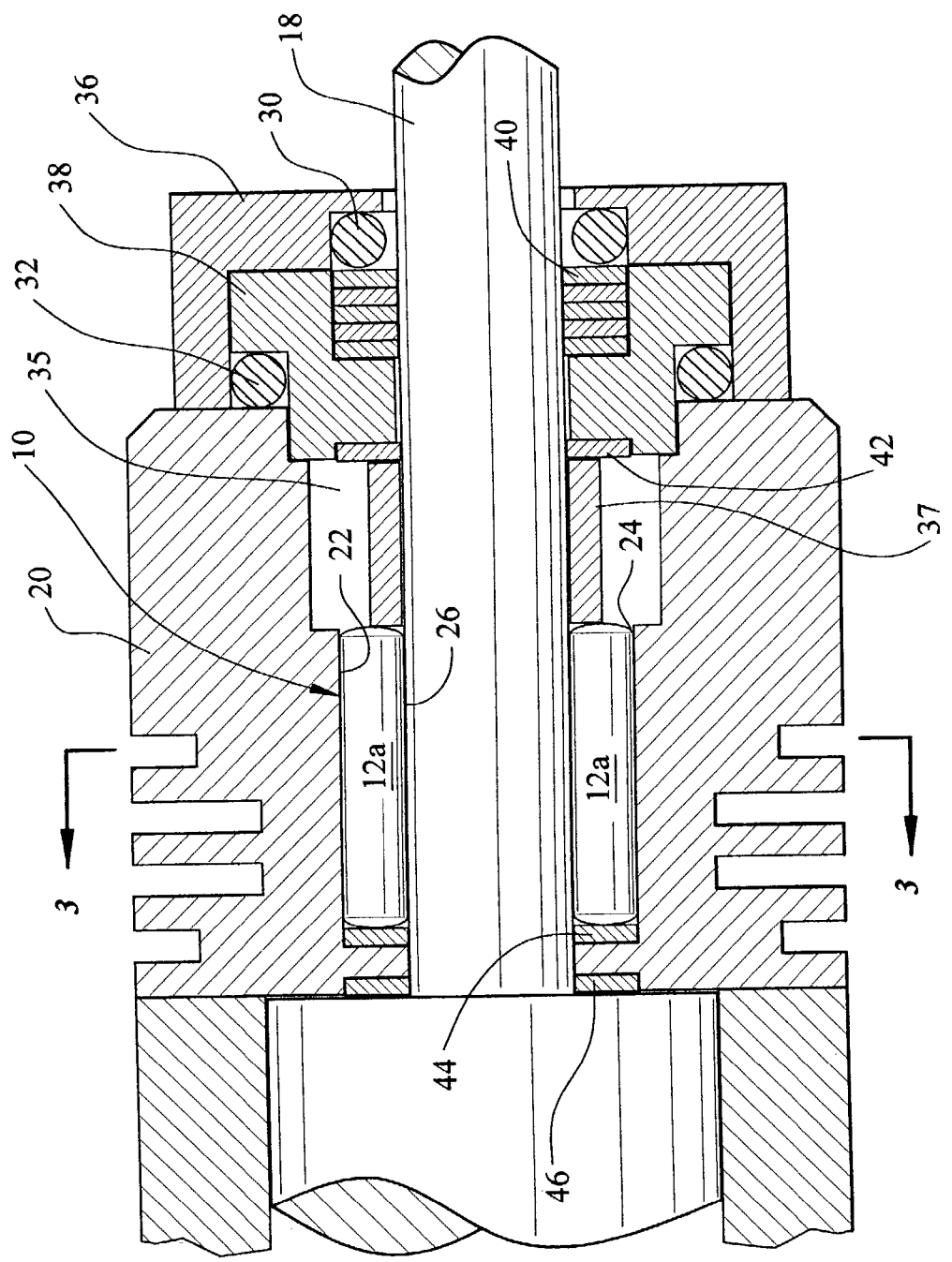
FIG. 1 is a fragmentary sectional view illustrating the details of this invention.
Figure 2:
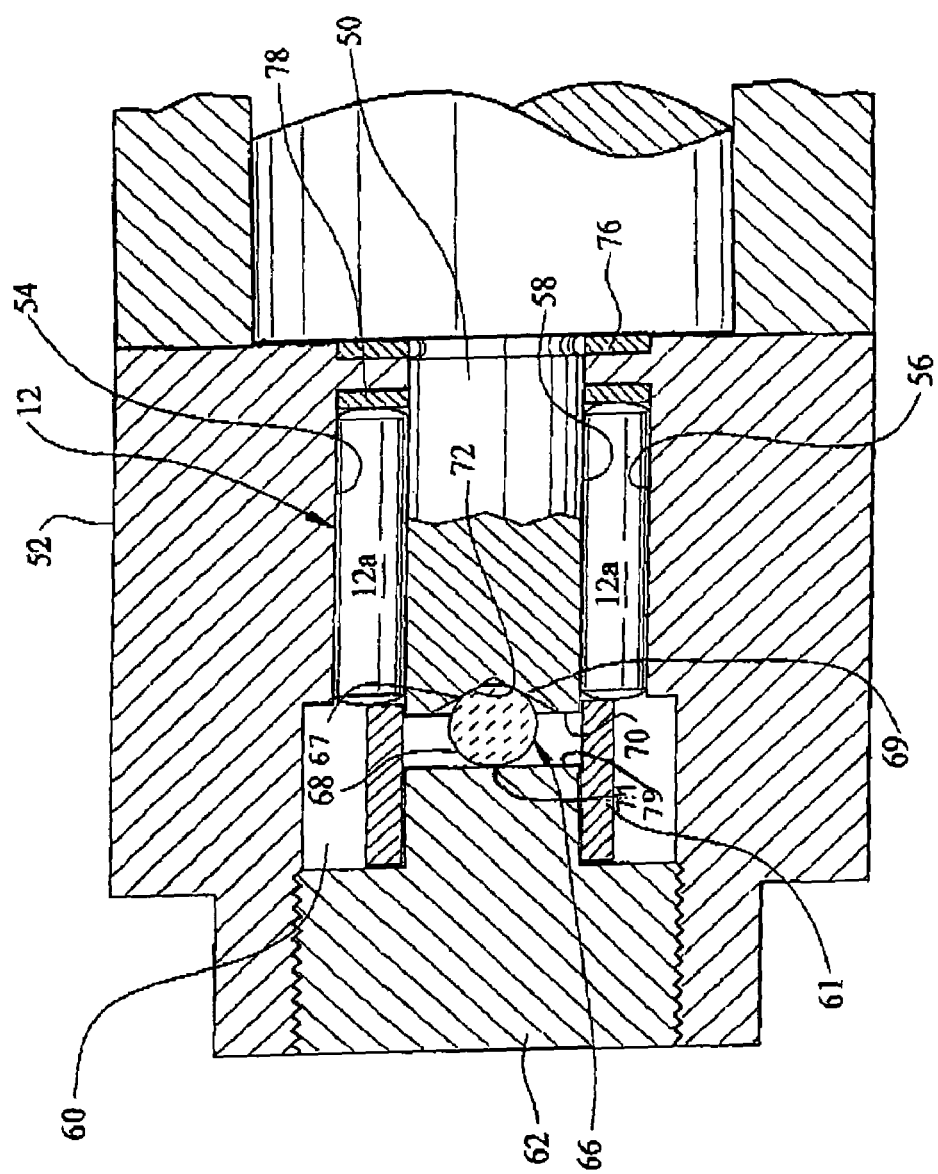
FIG. 2 is a fragmentary sectional view illustrating another embodiment of this invention.

This invention is best seen by referring to FIGS. 1-3 that illustrate the needle/roller bearing of this invention generally indicated by reference numeral 10 comprising a plurality of elongated rollers or needles 12 wherein adjacent needles 12 include alternate needles made from different materials. As noted in FIG. 3 the needle 12a is made from a metallic material and the needle 12b is made from a plastic material. A suitable metal material can be surgical stainless steel and a suitable plastic can be made from a polymer of polyimide resin and graphite composition. While these materials are preferred, it will be appreciated that other like materials can be utilized bearing in mind that alternate needles are made from different materials and that one of the alternate materials must be made from a plastic, rubber or other synthetic materials. It will also be appreciated that the number of needles 12 will always be even, i.e. the first needle or roller will be metal and the last needle or roller will be plastic or other synthetic material.

As seen in FIGS. 1 and 3 the needle bearing 10 consists of a plurality of rollers 12a and 12b circumferentially mounted about the rotating shaft 18 supported by the bearing in housing 20. It will be appreciated that the bearings are not mounted in either an outer race and inner race but rather are mounted in the bore 22 of housing 20 and bear against the annular surface 24 defining bore 22 and the outer surface 26 of shaft 18. Also from the foregoing it will be appreciated that the rollers are not mounted in a cage. The assembly can include a number of O-seals 30 and 32 suitably retained by the end cap 36 and the annular disk 38. Also suitable packing 40, 42, 44 and 46 may likewise be employed to provide a dirt free environment for the rotating mechanism. The cavity or compartment 35 serves to hold a grease or other lubricant for lubricating the moving parts. The annular spacer 37 prevents the rollers 12a from migrating into the compartment 35, assuring that the unit will have continuous lubrication and an extended life. Obviously, the invention is principally concerned with taking up the radial loads imposed by a rotating shaft and any other assembly could be easily substituted for the assembly just described. Obviously, the bearings can easily be inserted by removing the end cap 36 either with the shaft in place or the bearing can be inserted with the use of a viscous grease that would hold the bearing in place prior to the shaft being inserted.

As noted in FIG. 3 alternate bearings are made from different materials. One set of bearings preferably will be made from a stainless steel material and the other set of alternate bearings will be made from a polymer of polyimide resin and graphite composition. To appreciate this invention when utilized for medical instruments, the components are miniaturize. For example, the diameter of the needle 12 is substantially 0.04160 inches ("), the diameter of the bore 22 is substantially 0.17630" and the diameter of the shaft 18 is substantially 0.09310".

FIG. 2 is another embodiment of this invention illustrating the use of the needle bearing in conjunction with a thrust bearing. As indicated above, this invention is ideally suited to absorb the radial loads. In applications where it is necessary to absorb both radial and thrust loads, the needle bearing 12 (like elements bear the same reference numerals in all the Figs.) is mounted to support shaft 50 in the same manner that is shown in connection with FIGS. 1 and 3. The bearings 12a and 12b (only 12a being visible) is mounted between the shaft 50 and the housing 52. The bearings 12 bear against the inner surface 54 of the bore 56 and the outer surface 58 of shaft 50. It will be appreciated from the foregoing that the bearing does not include an inner race, outer race or cage. It is abundantly important for bearing 12 to be mounted such that the adjacent bearings 12a and 12b abut each other throughout the circumference of the bore 56.

In this embodiment, the cavity or compartment 60 formed on the end of housing 52 adjacent to bearing 12 is enclosed by the removable end cap 62 that is suitably threaded to the housing 52. The compartment 60 is filled with grease or lubricant and serves the same purpose as compartment 35 described in connection with the embodiment depicted in FIG. 1. The annular spacer 61 prevents the rollers 12a from migrating into the compartment 60. The thrust bearing generally indicated by reference numeral 66 is a spherically shaped ball 68 that is mounted between the end 79 of end cap 62 and the end 70 of shaft 50. The end 70 may include a conically shaped recess 72 to retain the spherical ball and transmit the axial loads from the shaft 50 to the housing 52. In this arrangement of thrust bearing 66, the axial loads are transmitted to ball 68 at the points of contact 67 and 69 and transmit the load through the ball to the point of contact 71 where the ball is in coincidence with the rotational axis and hence, at 0 revolution per minute. Suitable sealing means or packing 76, and 78 may be employed to seal the bearings 12 and 66 and lubricant from being contaminated from the ambient and leakage of lubricant.

What has been shown by this invention is a relatively inexpensive means for providing a needle bearing for efficaciously absorbing the radial loads of a relatively high speed surgical drill or instrument. The typical rotational speed of these instruments are 80,000 revolutions per minute. It will be appreciated further that the typical inner and outer races and the cage may be eliminated which obviously would otherwise contribute to the costs and the complexity of the assembly.

Although this invention has been shown and described with respect to detailed embodiments thereof, it will be appreciated and understood by those skilled in the art that various changes in form and detail thereof may be made without departing from the spirit and scope of the claimed invention.

It is claimed:

1. For a high speed surgical drill including a housing and a shaft supported in said housing, said shaft being supported for radial loads by a needle bearing having a plurality of rollers circumferentially mounted in a bore in said housing and bearing against the outer surface of said shaft, the adjacent roller of each of said plurality of rollers being mounted in contact relationship with each other, and alternate rollers of said plurality of rollers being made from a metallic material and the other alternate rollers being made from a non-metallic material.

2. For a high speed surgical drill as claimed in claim 1 wherein said rollers are mounted without an inner race and an outer race.

3. For a high speed surgical drill as claimed in claim 2 wherein said rollers are mounted without a cage.

4. For a high speed surgical drill as claimed in claim 3 wherein said metallic material is stainless steel and said non-metallic material is a polymer of polyimide resin.

5. In combination, a rotary drill having a housing, a shaft supported by needle bearing and thrust bearing mounted in said housing, said needle bearing having a plurality of rollers circumferentially mounted side by side for supporting a rotary shaft mounted in a bore in said housing wherein each roller of said plurality of rollers is mounted between the inner surface defining said bore and the outer surface of said shaft and bear there-against and wherein alternate rollers of said plurality of rollers are made from a metallic material and the other alternate rollers of said plurality of rollers are made from a plastic or synthetic material, a thrust bearing comprising a spherically-shaped ball mounted adjacent the end of said shaft having one portion bearing against said shaft and another portion bearing against said housing.

6. The combination of claim 5 wherein said metallic material is a stainless steel and said plastic or synthetic material is a polymer of polyimide resin.

7. The combination of claim 6 where the synthetic material is made from a polymer of polyimide resin and graphite composition.

8. For a high speed surgical rotary instrument including a housing and a rotary shaft supported in said housing, said shaft having an axial end and being supported for radial loads by a needle bearing and supported for axial loads by a ball bearing, said needle bearing having a plurality of rollers circumferentially mounted in a bore in said housing and bearing against the outer surface of said shaft and the inner surface of the bore, the adjacent roller of each of said plurality of rollers being mounted in contact relationship with each other, and alternate rollers of said plurality of rollers being made from a metallic material and the other alternate rollers being made from a non-metallic material and said ball bearing mounted in said bore and bearing against at the axial end of said shaft and said housing.

9. For a high speed surgical rotary instrument as claimed in claim 8 wherein said metallic material is a stainless steel and said non-metallic material is a polymer of polyimide resin.

10. For a high speed surgical rotary instrument as claimed in claim 9 including an end cap adjacent to said bore for sealing off said bore on one end of said housing, a conical slot having side surface, a portion of said ball bearing against said end cap and another portion of said ball bearing against the side surface of the conical slot formed on the axial end of the shaft and said ball being located such that the point of contact of the portion of said ball and said cap is in coincidence with the rotating axis of said shalt.

11. For a high speed surgical rotary instrument as claimed in claim 8 said metallic material is a stainless steel and said non-metallic material is a polymer of polyimide resin and graphite composition.

12. For a high speed surgical rotary instrument as claimed in claim 8 wherein said bore includes a first compartment for said plurality of rollers and a second compartment adjacent to said rollers for holding a lubricant, a spacer disposed in said second compartment between an end of each roller of said plurality of rollers and said end cap.

13. For a high speed surgical rotary instrument including a housing and a rotary shaft having a smaller diameter portion and a larger diameter portion, said smaller diameter portion being supported in said housing, said larger diameter portion being mounted adjacent to and downstream of said smaller diameter portion, said shaft being supported for radial loads by a needle bearing mounted in a bore in said housing and adjacent to said smaller diameter portion, the adjacent roller of each of said plurality of rollers being mounted in contact relationship with each other, and alternate rollers of said plurality of rollers being made from a metallic material and the other alternate rollers being made from a non-metallic material, a ball bearing, and said ball bearing mounted in said bore and bearing against at the axial end of said shaft and said housing.

14. For a high speed surgical rotary instrument as claimed in claim 13 including sealing means adjacent to said smaller diameter portion and one end of said roller bearing, and end cap affixed to said housing remote from said larger portion and having a bore in alignment with said smaller portion for receiving said smaller portion, said bore defining a first compartment for housing said roller bearing and an adjacent compartment for housing a lubricant, a spacer mounted in said adjacent compartment having one end bearing against said roller bearing and opposite end bearing against said end cap, seal means for said shaft and said end cap for sealing said lubricant.

15. For a high speed surgical rotary instrument as claimed in claim 14 wherein said metallic material is a stainless steel and said non-metallic material is a polymer of polyimide resin.

* * * * *